US007832042B2

(12) United States Patent
DePuydt et al.

(10) Patent No.: US 7,832,042 B2
(45) Date of Patent: Nov. 16, 2010

(54) BRUSH HEAD FOR TOOTHBRUSH

(75) Inventors: Joseph A. DePuydt, Quincy, MA (US); Bernhard Boland, Buchwaldstrasse (DE); Michael Stolper, Eschborn (DE); Thomas Fritsch, Eppstein (DE)

(73) Assignee: The Gillette Company, Boston, MA (US)

( * ) Notice: Subject to any disclaimer, the term of this patent is extended or adjusted under 35 U.S.C. 154(b) by 0 days.

(21) Appl. No.: 12/289,801

(22) Filed: Nov. 4, 2008

(65) Prior Publication Data
US 2009/0106923 A1    Apr. 30, 2009

Related U.S. Application Data

(63) Continuation of application No. 11/430,280, filed on May 9, 2006, now Pat. No. 7,448,107, which is a continuation of application No. 10/697,206, filed on Oct. 30, 2003, now abandoned, which is a continuation of application No. 10/456,769, filed on Jun. 6, 2003, now Pat. No. 6,760,946, which is a continuation of application No. 09/425,423, filed on Oct. 22, 1999, now Pat. No. 6,574,820.

(51) Int. Cl.
    *A46B 13/02*    (2006.01)
(52) U.S. Cl. .............................. 15/22.4; 15/22.1; 15/28; 15/167.1; 15/167.2; 15/201
(58) Field of Classification Search .................. 15/22.1, 15/28, 22.2, 22.4, 29, 23, 167.1, 167.2, 201
See application file for complete search history.

(56) References Cited

U.S. PATENT DOCUMENTS 793,587 A    6/1905    Johnson (Continued)

FOREIGN PATENT DOCUMENTS

CN    2271352    7/1996

(Continued)

OTHER PUBLICATIONS

Bader, "Review of Currently Available Battery-Operated Toothbrushes", *Compend. Contin. Educ. Dent.*, vol. 13, No. 12, p. 1162, 1164-1169.

(Continued)

*Primary Examiner*—Gary K Graham
(74) *Attorney, Agent, or Firm*—Charles P. Boukus, Jr.; George H. Leal

(57) ABSTRACT

An elongated toothbrush head defining a longitudinal axis includes a first brush member having a first brush support surface and a second brush member which is a pivot arm mounted for pivotal movement on the first brush member. The pivot arm has a second brush support surface including a first portion and a second portion which are joined together and include free ends which are spaced apart. The first portion and the second portion of the second brush support surface are capable of pivoting relative to the first brush support surface about an axis which extends transversely to the longitudinal axis of the head and laterally across the pivot arm. One or more teeth cleaning elements project from the first portion and the second portion and are inclined at an angle to the second brush support surface.

10 Claims, 8 Drawing Sheets

U.S. PATENT DOCUMENTS

| | | | |
|---|---|---|---|
| 1,212,001 A | 1/1917 | Baxter | |
| 1,255,028 A | 1/1918 | Leonard et al. | |
| 1,392,623 A | 10/1921 | Cheatham | 15/29 |
| 1,517,320 A | 12/1924 | Stoddart | |
| 1,553,456 A | 9/1925 | Metrakos | |
| 1,557,244 A | 10/1925 | Dominque | |
| 1,896,731 A | 2/1933 | Lippett | 15/28 |
| 1,911,973 A | 5/1933 | Ruse | 15/28 |
| 1,928,328 A | 9/1933 | Carpenter | |
| 1,981,688 A | 11/1934 | Conti | |
| 1,997,352 A | 4/1935 | Fleet | |
| 2,044,863 A | 6/1936 | Sticht | |
| 2,140,307 A | 12/1938 | Belaschk et al. | 15/28 |
| 2,172,624 A | 9/1939 | Robert | |
| 2,215,031 A | 9/1940 | Elmore | |
| 2,379,049 A | 6/1945 | Tompkins | |
| 2,435,421 A | 2/1948 | Blair | |
| 2,601,567 A | 6/1952 | Steinberg | |
| 3,115,652 A | 12/1963 | Zerbee | |
| 3,129,449 A | 4/1964 | Cyzer | |
| 3,159,859 A | 12/1964 | Rasmussen | |
| 3,160,902 A | 12/1964 | Aymar | |
| 3,178,754 A | 4/1965 | Cleverdon | |
| 3,195,537 A | 7/1965 | Blasi | |
| 3,242,516 A | 3/1966 | Cantor | |
| 3,270,360 A | 9/1966 | Kropp | 15/22.1 |
| 3,379,906 A | 4/1968 | Spohr | |
| 3,398,421 A | 8/1968 | Rashbaum | |
| 3,509,874 A | 5/1970 | Stillman | |
| 3,524,088 A | 8/1970 | Ryckman | |
| 3,538,530 A | 11/1970 | Stemme | |
| 3,588,936 A | 6/1971 | Duve | |
| 3,592,188 A | 7/1971 | Barnett | |
| 3,935,869 A | 2/1976 | Reinsch | |
| 3,945,076 A | 3/1976 | Sung | |
| 3,978,852 A | 9/1976 | Annoni | |
| 4,027,348 A | 6/1977 | Flowers et al. | |
| 4,156,620 A | 5/1979 | Clemens | 134/6 |
| 4,175,299 A | 11/1979 | Teague, Jr. et al. | |
| 4,274,173 A | 6/1981 | Cohen | |
| 4,326,314 A | 4/1982 | Moret et al. | |
| 4,346,492 A | 8/1982 | Solow | 15/22.1 |
| 4,397,055 A | 8/1983 | Cuchiara | |
| 4,545,087 A | 10/1985 | Nahum | 15/22.1 |
| 4,766,630 A | 8/1988 | Hegemann | 15/21.1 |
| 4,791,945 A | 12/1988 | Moriyama | |
| 4,795,347 A | 1/1989 | Maurer | |
| 4,845,795 A | 7/1989 | Crawford et al. | 15/22.1 |
| 4,974,278 A | 12/1990 | Hommann | |
| 4,989,287 A | 2/1991 | Scherer | |
| 4,995,131 A | 2/1991 | Takeda | |
| 5,007,127 A | 4/1991 | Paolo | 15/29 |
| 5,033,150 A | 7/1991 | Gross et al. | |
| 5,046,213 A | 9/1991 | Curtis et al. | 15/167.1 |
| 5,052,071 A | 10/1991 | Halm | 15/167.1 |
| 5,054,154 A | 10/1991 | Schiffer et al. | 15/167.1 |
| 5,068,939 A | 12/1991 | Holland | 15/22.1 |
| 5,070,567 A | 12/1991 | Holland | 15/28 |
| 5,077,855 A | 1/1992 | Ambasz | |
| 5,088,145 A | 2/1992 | Whitefield | 15/22.1 |
| 5,120,225 A | 6/1992 | Amit | |
| 5,138,734 A | 8/1992 | Chung | 15/28 |
| 5,145,369 A | 9/1992 | Lustig et al. | 433/118 |
| 5,170,525 A | 12/1992 | Cataro | |
| 5,177,826 A * | 1/1993 | Vrignaud et al. | 15/22.1 |
| 5,184,368 A | 2/1993 | Holland | 15/167.1 |
| 5,186,627 A | 2/1993 | Amit et al. | 433/216 |
| 5,226,206 A | 7/1993 | Davidovitz et al. | 15/22.1 |
| 5,253,382 A | 10/1993 | Beny | |
| 5,259,083 A | 11/1993 | Stansbury, Jr. | 15/22.1 |
| 5,276,932 A | 1/1994 | Byrd | |
| 5,301,381 A | 4/1994 | Klupt | 15/22.1 |
| 5,311,633 A | 5/1994 | Herzog et al. | |
| 5,321,866 A | 6/1994 | Klupt | |
| 5,323,504 A | 6/1994 | McCusker | 15/167.1 |
| 5,337,435 A | 8/1994 | Krasner et al. | 15/23 |
| 5,353,460 A | 10/1994 | Bauman | |
| 5,357,644 A | 10/1994 | Theriault | 15/22.1 |
| 5,359,747 A | 11/1994 | Amakasu | |
| 5,365,624 A | 11/1994 | Berns | 15/22.1 |
| 5,373,602 A | 12/1994 | Bang | 15/167.1 |
| 5,383,242 A | 1/1995 | Bigler et al. | |
| 5,398,366 A | 3/1995 | Bradley | |
| 5,404,608 A | 4/1995 | Hommann | |
| 5,416,942 A | 5/1995 | Baldacci et al. | 15/22.1 |
| 5,435,032 A | 7/1995 | McDougall | 15/22.1 |
| 5,446,939 A | 9/1995 | Park | 15/23 |
| 5,448,792 A | 9/1995 | Wiedemann et al. | |
| 5,450,646 A | 9/1995 | McHugh et al. | 15/22.1 |
| 5,465,444 A | 11/1995 | Bigler et al. | |
| 5,465,450 A | 11/1995 | Humphries | 15/167.1 |
| 5,493,747 A | 2/1996 | Inakagata et al. | |
| 5,499,420 A | 3/1996 | Boland | 15/22.1 |
| 5,500,970 A | 3/1996 | Maurer et al. | 15/22.1 |
| 5,504,958 A | 4/1996 | Herzog | |
| 5,504,959 A | 4/1996 | Yukawa et al. | 15/22.1 |
| 5,524,312 A | 6/1996 | Tan et al. | 15/22.1 |
| 5,528,786 A | 6/1996 | Porat et al. | |
| 5,546,626 A | 8/1996 | Chung | 15/167.1 |
| 5,573,020 A | 11/1996 | Robinson | 132/322 |
| 5,577,285 A | 11/1996 | Drossler | 15/22.1 |
| 5,617,601 A | 4/1997 | McDougall | |
| 5,617,603 A | 4/1997 | Mei | |
| 5,625,916 A | 5/1997 | McDougall | 15/28 |
| 5,652,990 A | 8/1997 | Driesen et al. | 15/28 |
| 5,679,991 A | 10/1997 | Wolf | |
| 5,687,442 A | 11/1997 | McLain | |
| 5,700,146 A | 12/1997 | Kucar | |
| 5,709,233 A | 1/1998 | Boland et al. | 132/322 |
| 5,715,556 A | 2/1998 | Chung | 15/22.1 |
| 5,727,273 A | 3/1998 | Pai | |
| 5,732,433 A | 3/1998 | Gocking et al. | |
| 5,738,575 A | 4/1998 | Bock | 433/216 |
| 5,765,254 A | 6/1998 | O'Halloran | 15/167.1 |
| 5,778,474 A | 7/1998 | Shek | 15/22.1 |
| 5,784,743 A | 7/1998 | Shek | |
| RE35,941 E | 11/1998 | Stansbury, Jr. | |
| 5,836,030 A | 11/1998 | Hazeu et al. | 15/22.1 |
| 5,839,148 A | 11/1998 | Volpenhein | 15/167.1 |
| 5,842,244 A | 12/1998 | Hilfinger et al. | |
| 5,842,245 A | 12/1998 | Pai | |
| 5,850,655 A | 12/1998 | Gocking et al. | 15/28 |
| 5,862,558 A | 1/1999 | Hilfinger et al. | |
| 5,867,856 A | 2/1999 | Herzog | |
| 5,898,967 A | 5/1999 | Wu et al. | 15/167.1 |
| 5,946,758 A | 9/1999 | Hohlbein et al. | 15/167.1 |
| 5,956,797 A | 9/1999 | Wilson | 15/167.1 |
| 5,974,615 A | 11/1999 | Schwarz-Hartmann et al. | |
| 5,987,690 A | 11/1999 | Heuler | 15/167.1 |
| 6,000,083 A | 12/1999 | Blaustein et al. | |
| 6,003,189 A | 12/1999 | Falleiros | 15/167.1 |
| 6,032,313 A | 3/2000 | Tsang | 15/22.1 |
| 6,073,299 A | 6/2000 | Hohlbein | 15/167.1 |
| 6,106,290 A | 8/2000 | Weissman | 433/132 |
| 6,138,310 A | 10/2000 | Porper et al. | |
| 6,178,579 B1 | 1/2001 | Blaustein et al. | |
| 6,178,582 B1 | 1/2001 | Halm | 15/167.1 |
| 6,189,693 B1 | 2/2001 | Blaustein et al. | |
| 6,195,828 B1 | 3/2001 | Fritsch | |
| 6,237,178 B1 | 5/2001 | Krammer et al. | |
| 6,308,359 B2 | 10/2001 | Fritsch et al. | |
| 6,311,837 B1 | 11/2001 | Blaustein et al. | |
| 6,347,425 B1 | 2/2002 | Fattori et al. | |
| 6,360,395 B2 | 3/2002 | Blaustein et al. | |

| | | |
|---|---|---|
| 6,371,294 B1 | 4/2002 | Blaustein et al. |
| 6,408,473 B1 | 6/2002 | Kessler .................... 15/104.94 |
| 6,421,865 B1 | 7/2002 | McDougall |
| 6,421,866 B1 | 7/2002 | McDougall |
| 6,434,773 B1 | 8/2002 | Kuo |
| 6,446,294 B1 | 9/2002 | Specht |
| 6,453,498 B1 | 9/2002 | Wu |
| 6,463,615 B1 | 10/2002 | Gruber et al. |
| 6,510,575 B2 | 1/2003 | Calabrese |
| 6,536,066 B2 | 3/2003 | Dickie |
| 6,546,585 B1 | 4/2003 | Blaustein et al. |
| 6,564,940 B2 | 5/2003 | Blaustein et al. |
| 6,574,820 B1 | 6/2003 | DePuydt et al. ................. 15/28 |
| 6,623,698 B2 | 9/2003 | Kuo |
| 6,675,428 B2 | 1/2004 | Halm ........................ 15/167.1 |
| 6,725,490 B2 | 4/2004 | Blaustein et al. |
| 6,760,946 B2 | 7/2004 | DePuydt et al. .............. 15/22.4 |
| 6,836,917 B2 | 1/2005 | Blaustein et al. |
| 6,889,401 B2 | 5/2005 | Fattori et al. ................. 15/22.1 |
| 6,892,412 B2 | 5/2005 | Gatzemeyer et al. |
| 6,892,413 B2 | 5/2005 | Blaustein et al. |
| 6,928,685 B1 | 8/2005 | Blaustein et al. |
| 6,932,216 B2 | 8/2005 | Blaustein et al. |
| 6,944,901 B2 | 9/2005 | Gatzemeyer et al. |
| 6,952,854 B2 | 10/2005 | Blaustein et al. |
| 6,966,093 B2 | 11/2005 | Eliav et al. |
| 6,983,507 B2 | 1/2006 | McDougall |
| 6,996,870 B2 | 2/2006 | Hohlbein ..................... 15/110 |
| 7,124,461 B2 | 10/2006 | Blaustein et al. |
| 7,137,163 B2 | 11/2006 | Gatzemeyer et al. |
| 7,140,058 B2 | 11/2006 | Gatzemeyer et al. |
| 7,140,059 B2 | 11/2006 | Scherl |
| 7,150,061 B2 | 12/2006 | Kwong |
| 7,162,764 B2 | 1/2007 | Drossler et al. |
| 7,225,494 B2 | 6/2007 | Chan et al. |
| 7,258,747 B2 | 8/2007 | Vago et al. |
| 7,302,726 B2 | 12/2007 | Braun |
| 7,356,866 B2 | 4/2008 | Chan |
| 7,386,904 B2 | 6/2008 | Fattori |
| 7,392,562 B2 | 7/2008 | Boland et al. |
| 7,421,753 B2 | 9/2008 | Chan et al. |
| 7,430,777 B2 | 10/2008 | Scherl |
| 7,430,778 B2 | 10/2008 | Gatzemeyer et al. |
| 7,448,107 B2 | 11/2008 | DePuydt et al. .............. 15/22.1 |
| 7,451,514 B2 | 11/2008 | Blaustein et al. |
| 7,520,016 B2 | 4/2009 | Kressner |
| 7,552,497 B2 | 6/2009 | Gatzemeyer et al. |
| 2001/0001334 A1* | 5/2001 | Gruber et al. ................. 15/22.1 |
| 2002/0017474 A1 | 2/2002 | Blaustein et al. |
| 2002/0020645 A1 | 2/2002 | Blaustein et al. |
| 2002/0029988 A1 | 3/2002 | Blaustein et al. |
| 2002/0032941 A1 | 3/2002 | Blaustein et al. |
| 2002/0038772 A1 | 4/2002 | Blaustein et al. |
| 2002/0059685 A1 | 5/2002 | Paffrath |
| 2002/0078514 A1 | 6/2002 | Blaustein et al. |
| 2002/0138926 A1 | 10/2002 | Brown, Jr. |
| 2002/0152564 A1 | 10/2002 | Blaustein et al. |
| 2003/0066145 A1 | 4/2003 | Prineppi |
| 2003/0074751 A1 | 4/2003 | Wu |
| 2003/0084525 A1 | 5/2003 | Blaustein et al. |
| 2003/0084526 A1 | 5/2003 | Brown et al. |
| 2003/0084527 A1 | 5/2003 | Brown et al. |
| 2003/0140435 A1 | 7/2003 | Eliav et al. |
| 2003/0140437 A1 | 7/2003 | Eliav et al. |
| 2003/0154567 A1 | 8/2003 | Drossler et al. |
| 2003/0163881 A1 | 9/2003 | Driesen et al. |
| 2003/0163882 A1 | 9/2003 | Blaustein et al. |
| 2003/0182746 A1 | 10/2003 | Fattori et al. |
| 2003/0196283 A1 | 10/2003 | Eliav et al. |
| 2003/0213075 A1 | 11/2003 | Hui et al. |
| 2003/0226223 A1 | 12/2003 | Chan |
| 2004/0045105 A1 | 3/2004 | Eliav et al. |
| 2004/0060137 A1 | 4/2004 | Eliav |
| 2004/0074026 A1 | 4/2004 | Blaustein et al. |
| 2004/0083566 A1 | 5/2004 | Blaustein |
| 2004/0088807 A1 | 5/2004 | Blaustein et al. |
| 2004/0143917 A1 | 7/2004 | Ek |
| 2004/0168272 A1 | 9/2004 | Prineppi |
| 2004/0177458 A1 | 9/2004 | Chan et al. |
| 2004/0177462 A1 | 9/2004 | Brown, Jr. |
| 2005/0000043 A1 | 1/2005 | Chan et al. |
| 2005/0000045 A1 | 1/2005 | Blaustein |
| 2005/0091771 A1 | 5/2005 | Blaustein et al. |
| 2005/0102776 A1 | 5/2005 | Mathur |
| 2005/0155167 A1 | 7/2005 | Gall et al. |
| 2005/0268409 A1 | 12/2005 | Blaustein et al. |
| 2005/0278874 A1 | 12/2005 | Blaustein et al. |
| 2006/0032006 A1 | 2/2006 | Brown et al. |
| 2006/0048314 A1 | 3/2006 | Kressner |
| 2006/0048315 A1 | 3/2006 | Chan et al. |
| 2006/0137118 A1 | 6/2006 | Blaustein |
| 2006/0254006 A1 | 11/2006 | Blaustein et al. |
| 2006/0254007 A1 | 11/2006 | Banning |
| 2007/0251033 A1 | 11/2007 | Brown et al. |
| 2008/0010761 A1 | 1/2008 | Blaustein et al. |
| 2008/0016633 A1 | 1/2008 | Blaustein et al. |
| 2008/0078040 A1 | 4/2008 | Braun |
| 2009/0106923 A1 | 4/2009 | DePuydt et al. |

FOREIGN PATENT DOCUMENTS

| | | |
|---|---|---|
| CN | 2236827 Y | 10/1996 |
| CN | 2271353 | 10/1996 |
| CN | 2274947 Y | 2/1998 |
| CN | 330411 | 4/1998 |
| CN | 1187341 A | 7/1998 |
| CN | 2324987 | 6/1999 |
| CN | 2324988 | 6/1999 |
| CN | 2681701 Y | 3/2005 |
| DE | 3406112 | 8/1985 |
| DE | 3544256 | 8/1987 |
| DE | 4003305 | 8/1991 |
| DE | 4412301 | 10/1995 |
| DE | 29600236 | 4/1996 |
| DE | 29613608 | 11/1996 |
| DE | 29618755 | 3/1997 |
| DE | 29517610 | 4/1997 |
| DE | 19701964 | 7/1998 |
| DE | 298 09 977 | 2/1999 |
| DE | 19802904 | 7/1999 |
| DE | 19803311 | 8/1999 |
| EP | 259648 | 3/1988 |
| EP | 0488971 | 6/1992 |
| EP | 0613666 A1 | 9/1994 |
| EP | 1053721 | 11/2000 |
| EP | 1059049 | 12/2000 |
| GB | 2247297 | 2/1992 |
| GB | 2290224 | 12/1995 |
| GB | 2319170 | 5/1998 |
| JP | 40-8743 | 8/1965 |
| JP | 57-89810 | 6/1982 |
| JP | 2-19241 | 2/1990 |
| JP | 02-218309 | 8/1990 |
| JP | 5146314 | 11/1991 |
| JP | 05-146313 | 6/1993 |
| JP | 05-146314 | 6/1993 |
| JP | 7-116020 | 5/1995 |
| JP | 7-116021 | 5/1995 |
| JP | 7-116023 | 5/1995 |
| JP | 07-116024 | 5/1995 |
| JP | 7-93892 | 10/1995 |
| JP | 8-322641 | 10/1996 |
| JP | 9-294631 | 11/1997 |
| JP | 10-66704 | 3/1998 |
| JP | H10-66704 | 3/1998 |
| JP | 2804940 | 7/1998 |

| | | |
|---|---|---|
| KR | 1984-0004668 | 9/1984 |
| KR | 1986-0001137 | 6/1986 |
| KR | 1994-0013418 | 7/1994 |
| KR | 1995-0002814 | 2/1995 |
| KR | 1995-0010820 | 5/1995 |
| KR | 1997-0000408 | 1/1997 |
| KR | 1997-0000409 | 1/1997 |
| KR | 1995-0024551 | 4/1998 |
| KR | 143460 | 4/1998 |
| TW | 257968 | 6/1905 |
| TW | 233472 | 5/1983 |
| TW | 256049 | 1/1993 |
| TW | 238504 | 6/1993 |
| TW | 253174 | 7/1994 |
| TW | 294031 | 11/1994 |
| TW | 239964 | 2/1995 |
| TW | 309753 | 7/1997 |
| TW | 330411 | 4/1998 |
| TW | 406557 | 9/2000 |
| WO | WO 94/28823 | 12/1994 |
| WO | WO 00/74592 | 12/2000 |
| WO | WO 00/78244 | 12/2000 |
| WO | WO 01/06946 | 2/2001 |
| WO | WO 01/06947 | 2/2001 |
| WO | WO 01/21094 | 3/2001 |
| WO | WO 01/43586 | 6/2001 |
| WO | WO 02/102187 A1 | 12/2002 |
| WO | WO 03/020159 | 3/2003 |
| WO | WO 2004/045448 A1 | 6/2004 |

OTHER PUBLICATIONS

U.S. Appl. No. 10/237,902, filed Sep. 9, 2002 entitled Topper for Power Toothbrush and Method for Forming the Same, all pages.
Photographs of electric toothbrush of BioBrush Industries (22 photographs).
Photos of Electric Toothbrush Head Refill.
PCT International Search report dated Sep. 26, 2007.
Office Action for U.S. Appl. No. 10/903,222; dated Apr. 11, 2005.
Office Action for U.S. Appl. No. 10/903,222; dated Oct. 19, 2004.
Office Action for U.S. Appl. No. 11/200,680; dated Sep. 22, 2005.
Office Action for U.S. Appl. No. 11/358,582; dated Mar. 17, 2008.
Office Action for U.S. Appl. No. 11/358,582; dated Apr. 14, 2006.
Office Action for U.S. Appl. No. 11/358,582; dated Apr. 17, 2007.
Advisory Action for U.S. Appl. No. 11/358,582; dated Jun. 9, 2008.
Advisory Action for U.S. Appl. No. 11/358,582; dated Jul. 27, 2007.
Office Action for U.S. Appl. 11/358,582; dated Sep. 5, 2008.
Office Action for U.S. Appl. No. 11/358,582; dated Sep. 6, 2007.
Office Action for U.S. Appl. No. 11/358,582; dated Sep. 29, 2006.
Office Action for U.S. Appl. No. 10/676,955; dated Jan. 24, 2005.
Office Action for U.S. Appl. No. 10/676,955; dated Jul. 12, 2005.
Office Action for U.S. Appl. No. 10/676,955; dated Jul. 29, 2004.
Office Action for U.S. Appl. No. 10/927,845; dated Dec. 28, 2004.
Office Action for U.S. Appl. No. 10/929,288; dated Mar. 18, 2005.
Office Action for U.S. Appl. No.10/929,288; dated Aug. 24, 2005.
Office Action for U.S. Appl. No. 11/514,742; dated Mar. 17, 2008.
Office Action for U.S. Appl. No. 11/514,742; dated Aug. 17, 2007.
Office Action for U.S. Appl. No. 11/514,742; dated Apr. 10, 2008.
Office Action for U.S. Appl. No. 11/006,972; dated Mar. 24, 2005.
Office Action for U.S. Appl. No. 10/896,540; dated Oct. 4, 2004.
Office Action for U.S. Appl. No. 11/414,908; dated May 23, 2007.
Office Action for U.S. Appl. No. 11/801,000; dated Jun. 20, 2008.
Office Action for U.S. Appl. No. 11/801,000; dated Sep. 26, 2008.
Office Action for U.S. Appl. No. 11/801,000; dated Oct. 26, 2007.
Office Action for U.S. Appl. No. 11/801,000; dated Dec. 5, 2008.
Office Action for U.S. Appl. No. 10/308,959; dated Feb. 16, 2006.
Advisory Action for U.S. Appl. No. 11/486,725; dated Jan. 28, 2008.
Office Action for U.S. Appl. No. 11/486,725; dated Jan. 28, 2009.
Office Action for U.S. Appl. No. 11/486,725; dated Jan. 29, 2007.
Office Action for U.S. Appl. No. 11/486,725; dated Apr. 10, 2008.
Office Action for U.S. Appl. No. 11/486,725; dated Aug. 13, 2007.
Office Action for U.S. Appl. No. 11/893,469; dated Oct. 14, 2008.
Office Action for U.S. Appl. No. 11/893,469; dated Dec. 18, 2008.
Office Action for U.S. Appl. No. 11/410,808; dated Feb. 15, 2007.
Office Action for U.S. Appl. No. 11/410,808; dated Jul. 17, 2007.
Office Action for U.S. Appl. No. 11/015,111; dated Nov. 24, 2008.
Office Action for U.S. Appl. No. 11/220,219; dated Oct. 20, 2008.
Office Action for U.S. Appl. No. 10/367,373; dated Mar. 9, 2004.
Office Action for U.S. Appl. No. 09/425,423; dated Jan. 31, 2002.
Office Action for U.S. Appl. No. 09/425,423; dated Aug. 14, 2002.
Office Action for U.S. Appl. No. 10/331,799; dated Apr. 19, 2005.
Office Action for U.S. Appl. No. 10/331,799; dated Oct. 14, 2005.
Office Action for U.S. Appl. No. 10/331,799; dated Feb. 23, 2006.
Office Action for U.S. Appl. No. 11/295,907; dated Jun. 5, 2009.
Office Action for U.S. Appl. No. 09/993,167; dated Dec. 18, 2002.
Office Action for U.S. Appl. No. 09/993,167; dated Apr. 16, 2003.

* cited by examiner

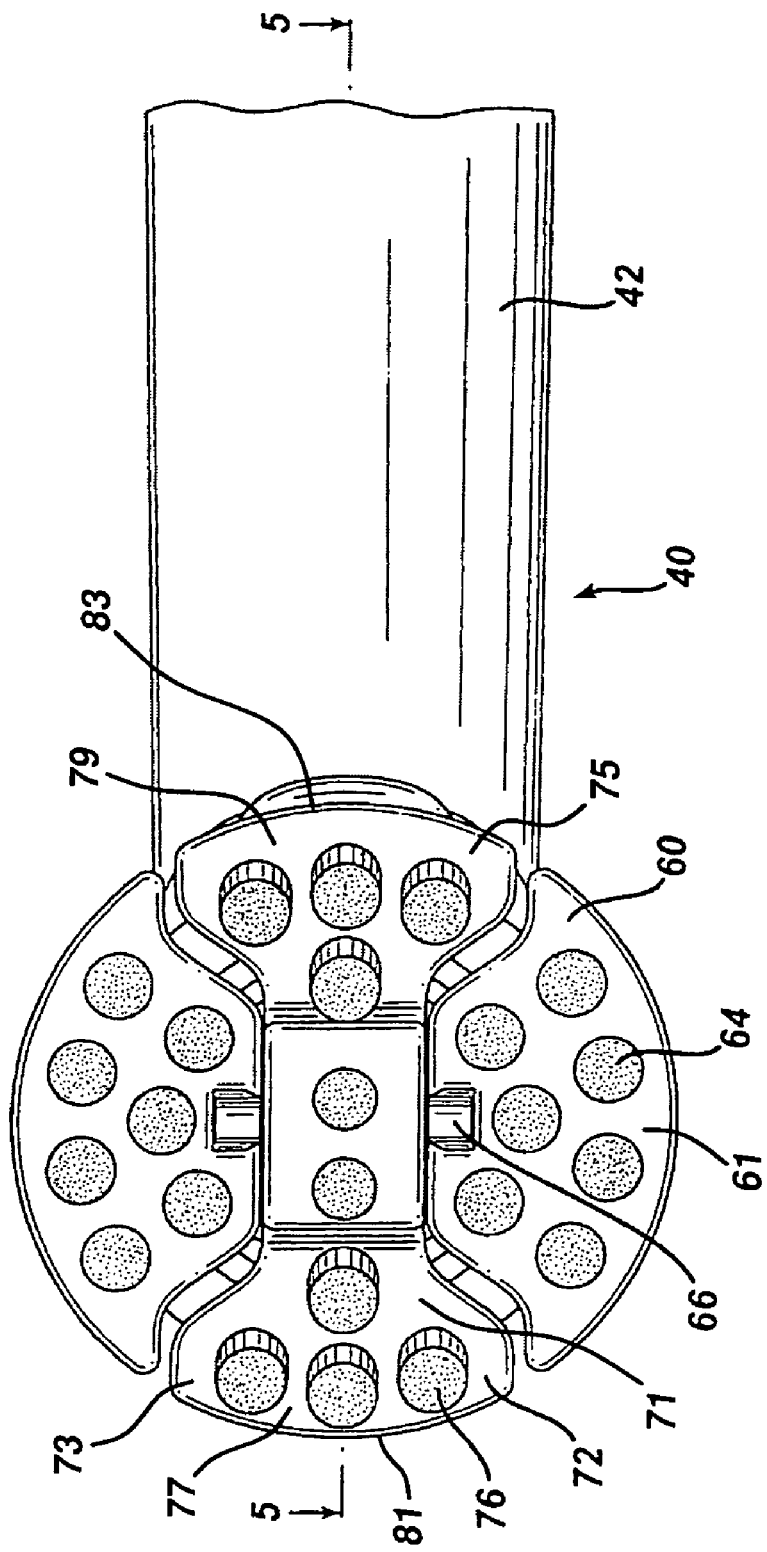

BRUSH HEAD FOR TOOTHBRUSH

CROSS-REFERENCE TO RELATED APPLICATIONS

This application is a continuation of U.S. patent application Ser. No. 11/430,280 filed on May 9, 2006 now U.S. Pat. No. 7,448,107 which is a continuation of U.S. patent application Ser. No. 10/697,206 filed on Oct. 30, 2003 now abandoned which is a continuation of U.S. patent application Ser. No. 10/456,769 filed on Jun. 6, 2003 (U.S. Pat. No. 6,760,946) which is a continuation of U.S. patent application Ser. No. 09/425,423 filed on Oct. 22, 1999 (U.S. Pat. No. 6,574,820).

FIELD OF THE INVENTION

The invention relates generally to the field of oral care, and in particular to toothbrushes. More specifically, the invention relates to a brush head for a toothbrush.

BACKGROUND OF THE INVENTION

U.S. Pat. No. 5,577,285 (the '285 patent) discloses an electric toothbrush with a rotary bristle supporting structure. In one embodiment of the invention shown in FIG. 6, the brush head is driven such that an outer ring of bristles 45a and an inner ring of bristles 45b are moved in an alternating rotary motion in opposite directions. While such an arrangement is beneficial for cleaning, for example, the bucal or lingual tooth surfaces, the lack of motion of any of the bristles in an up and down pattern results in a less than optimal cleaning of the inter-dental tooth surfaces.

FIG. 9 of the '285 patent discloses an additional embodiment of the invention in which all of the bristles 45 are rotated about an axis 54 while also being moved in an up and down motion parallel to this axis. This embodiment will provide enhanced cleaning of the inter-dental tooth surfaces. However, the fact that all of the bristles are moved up and down limits the depth of penetration that the bristles can obtain between the teeth. This is because while some of the bristles are trying to penetrate between the teeth, others are pressing against, for example, the bucal tooth surface, thus limiting the motion of the brush head towards the teeth.

SUMMARY OF THE INVENTION

The present invention is directed to overcoming one or more of the problems set forth above. Briefly summarized, according to one aspect of the present invention, a head for an electric toothbrush, includes a first bristle support which is rotatable about an axis and a plurality of first bristles extending from the first bristle support. A second bristle support includes a plurality of second bristles extending from a surface of the second bristle support at an acute angle to the surface.

These and other aspects, objects, features and advantages of the present invention will be more clearly understood and appreciated from a review of the following detailed description of the preferred embodiments and appended claims, and by reference to the accompanying drawings.

BRIEF DESCRIPTION OF THE DRAWINGS

FIG. 4 is a top plan view of a second embodiment of an electric toothbrush head;

DETAILED DESCRIPTION OF THE INVENTION

Figure 1:
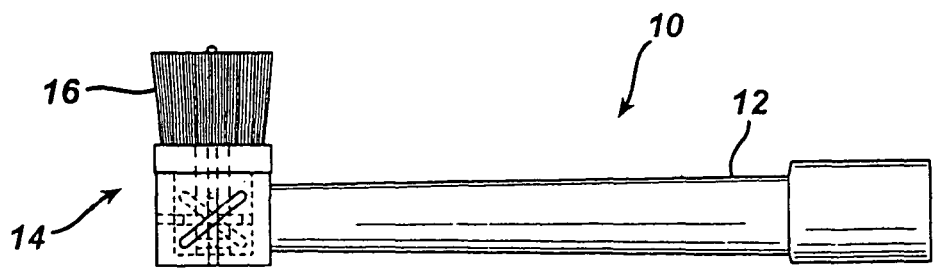
FIG. 1 is a side view of an electric toothbrush head attached to a brush handle/drive.

Beginning with FIG. 1, an electric toothbrush head 10 includes a neck 12 which is connected to a bristle support 14. Bristles 16 on support 14 are oscillated in a rotary movement through an arc of between about +−15 to 90 degrees, more preferably +−20 to 50 degrees as in a conventional electric toothbrush.

Figure 2:
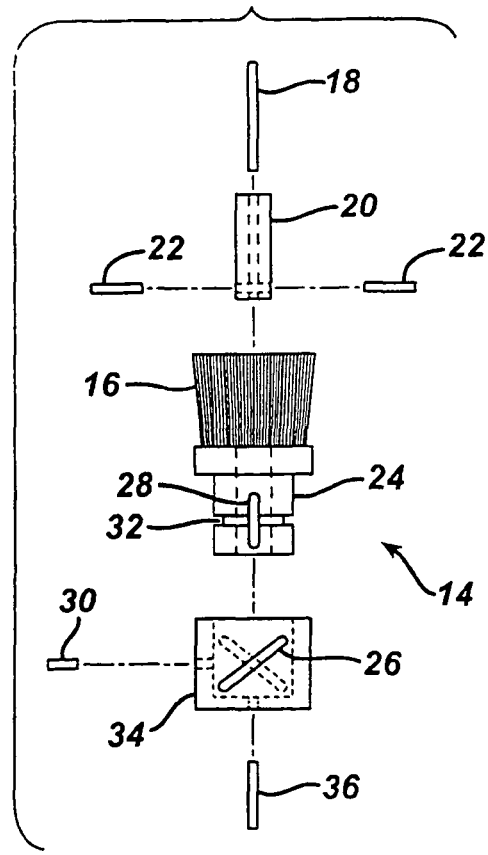
FIG. 2 is an exploded side view of the toothbrush head.

FIG. 2 shows support 14 in an exploded side view. An interdental probe 18 is secured to a slider core 20 in the center of bristles 16. Probe 18 can be a single large bristle or a tuft of much smaller bristles. Alternatively, core 20 can be enlarged to accommodate a plurality of probes (not shown), one of which may be positioned in the center of the core (as in FIG. 1), with the remainder of the probes being positioned on the core away from its center.

A pair of cam follower pins 22 are secured to opposite sides of the lower portion of core 20. Core 20 is positioned inside of a brush base 24 such that pins 22 are forced to ride along respective cam tracks 26 as well as respective vertical slider tracks 28 (one slider track is hidden behind the other). A retaining pin 30 rides in a track 32 to retain base 24 within a housing 34. A guide/rotation pin 36 passes through a hole in the bottom of housing 34 and is secured to base 24.

Figure 3A:
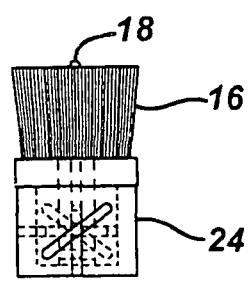
FIG. 3A is a side view of the head with a central bristle in a retracted position.
Figure 3B:
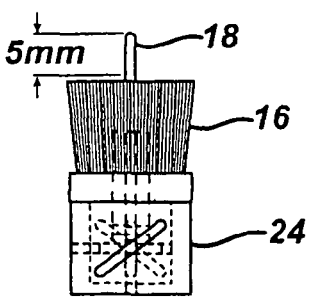
FIG. 3B is a side view of the head with a central bristle in an extended position.
Figure 5:
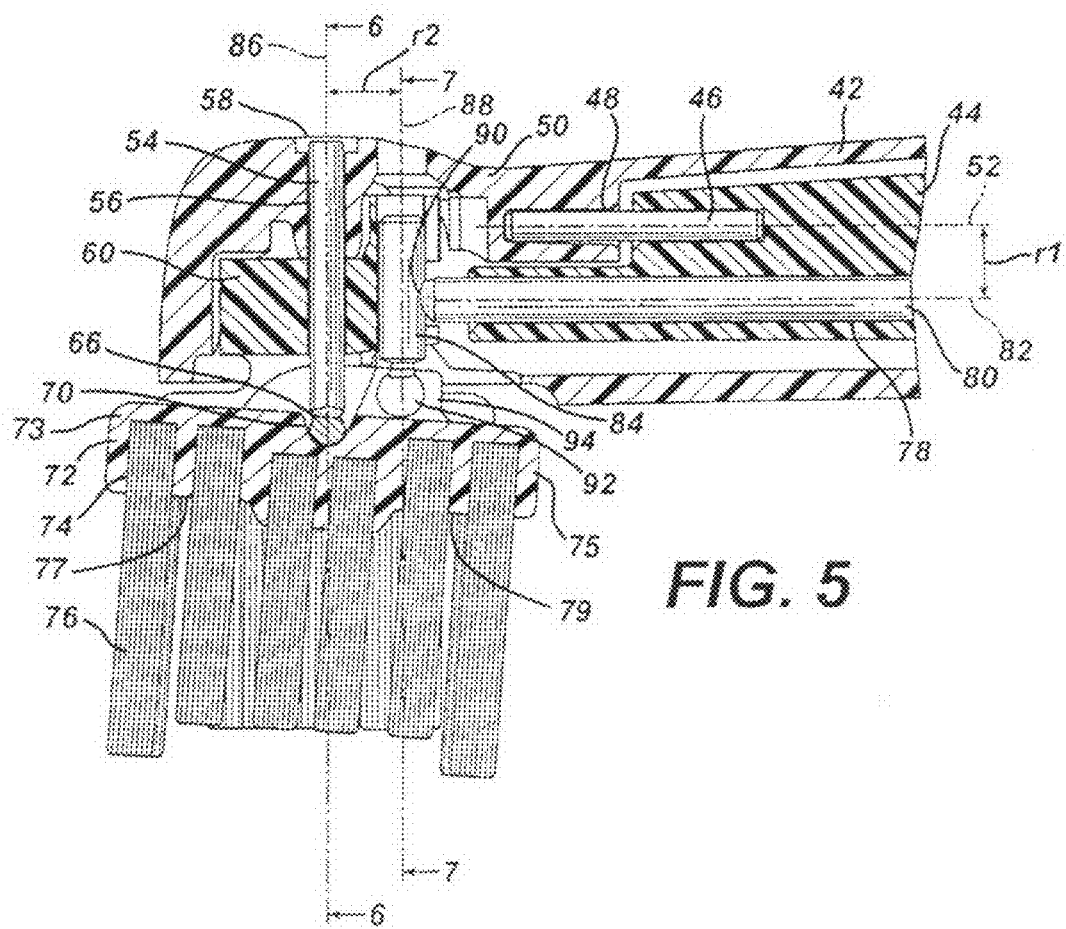
FIG. 5 is a sectional view of FIG. 4 taken along the lines 5-5.
Figure 6:
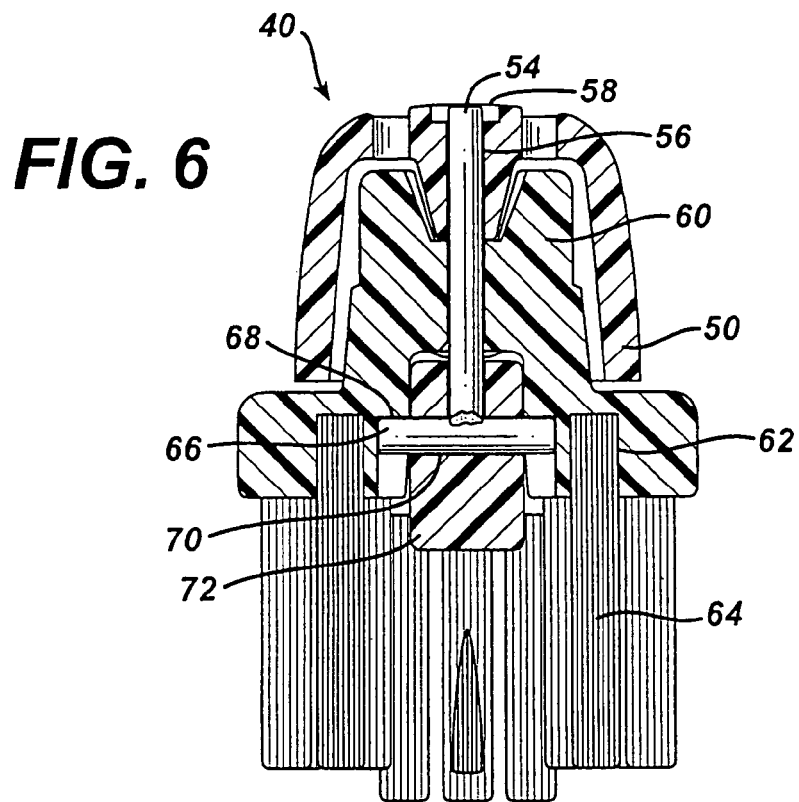
FIG. 6 is a sectional view of FIG. 5 taken along the lines 6-6.
Figure 7:
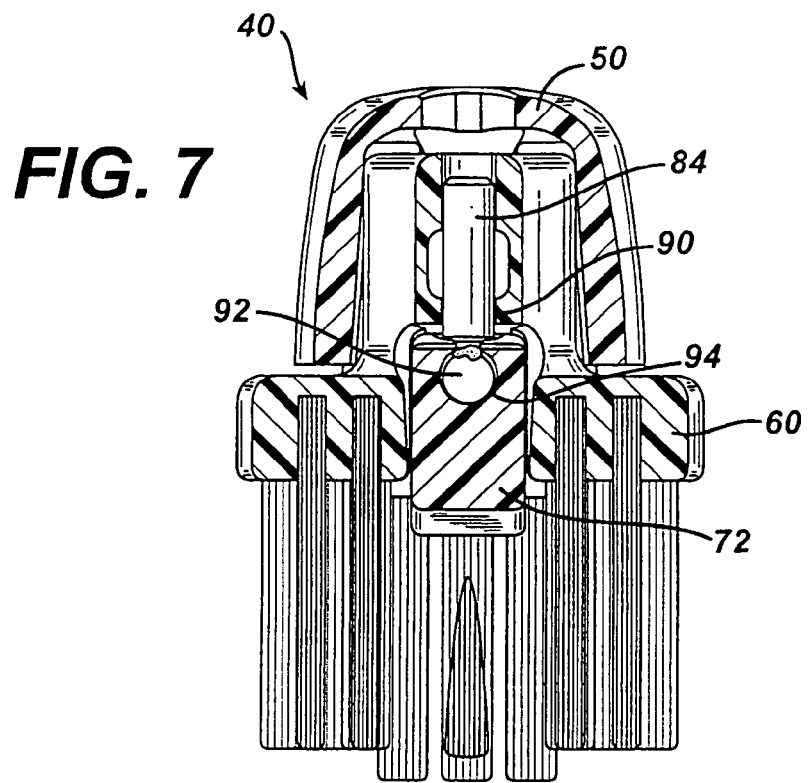
FIG. 7 is a sectional view of FIG. 5 taken along the lines 7-7.
Figure 8:
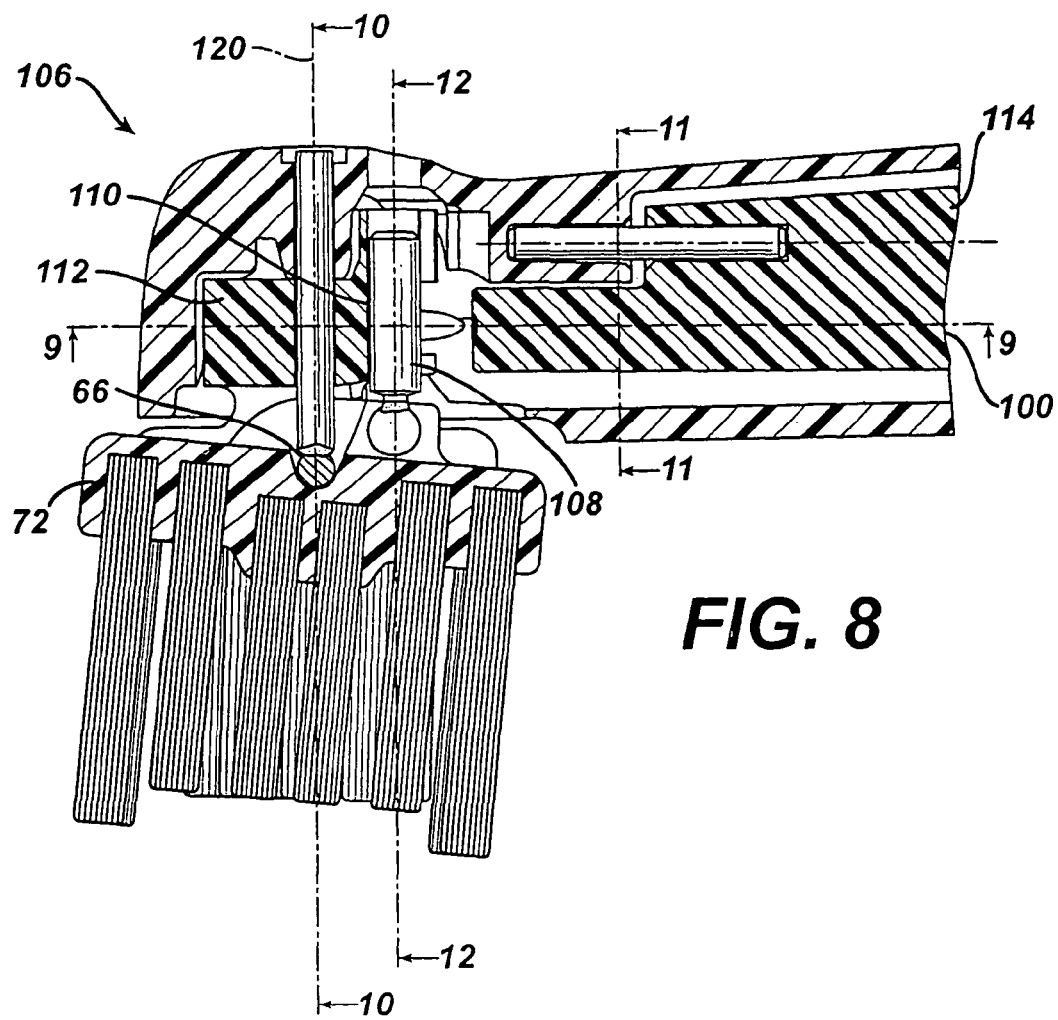
FIG. 8 is a sectional view similar to FIG. 5 of a third embodiment of the invention.
Figure 9:
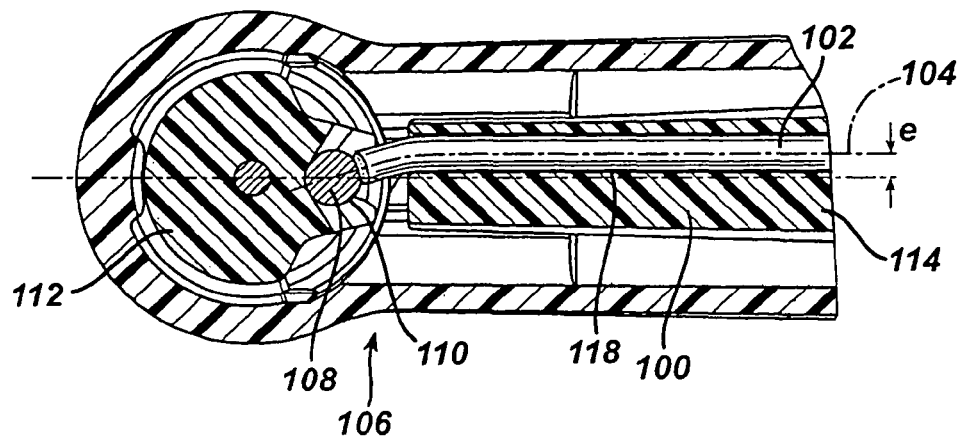
FIG. 9 is a sectional view of FIG. 8 taken along the lines 9-9.
Figure 10:
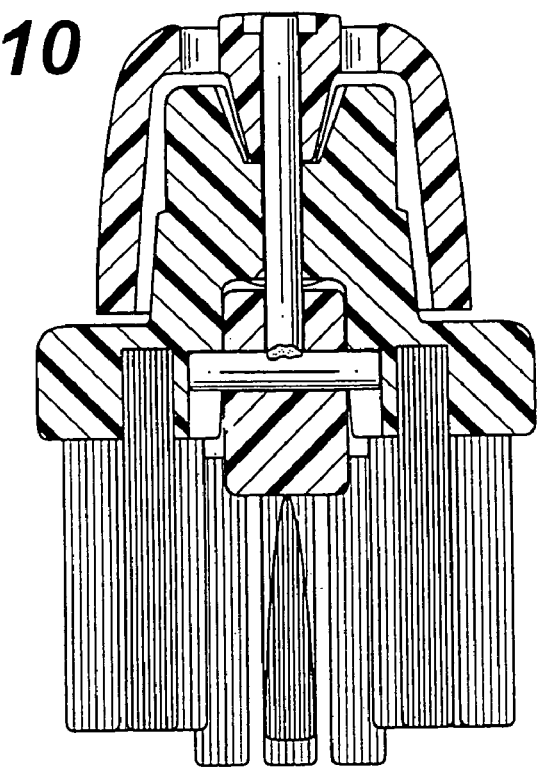
FIG. 10 is a sectional view of FIG. 8 taken along the lines 10-10.
Figure 11:
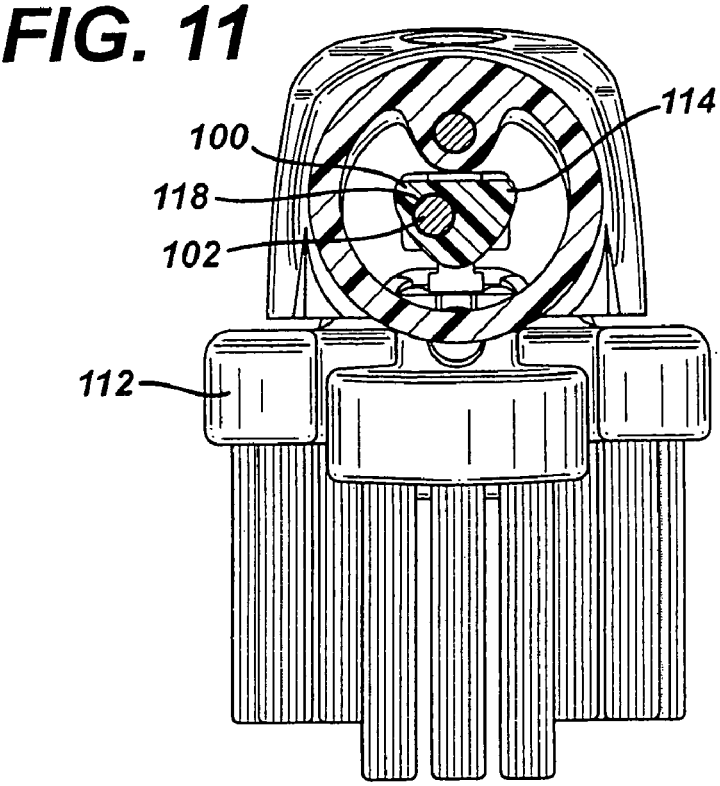
FIG. 11 is a sectional view of FIG. 8 taken along the lines 11-11.
Figure 12:
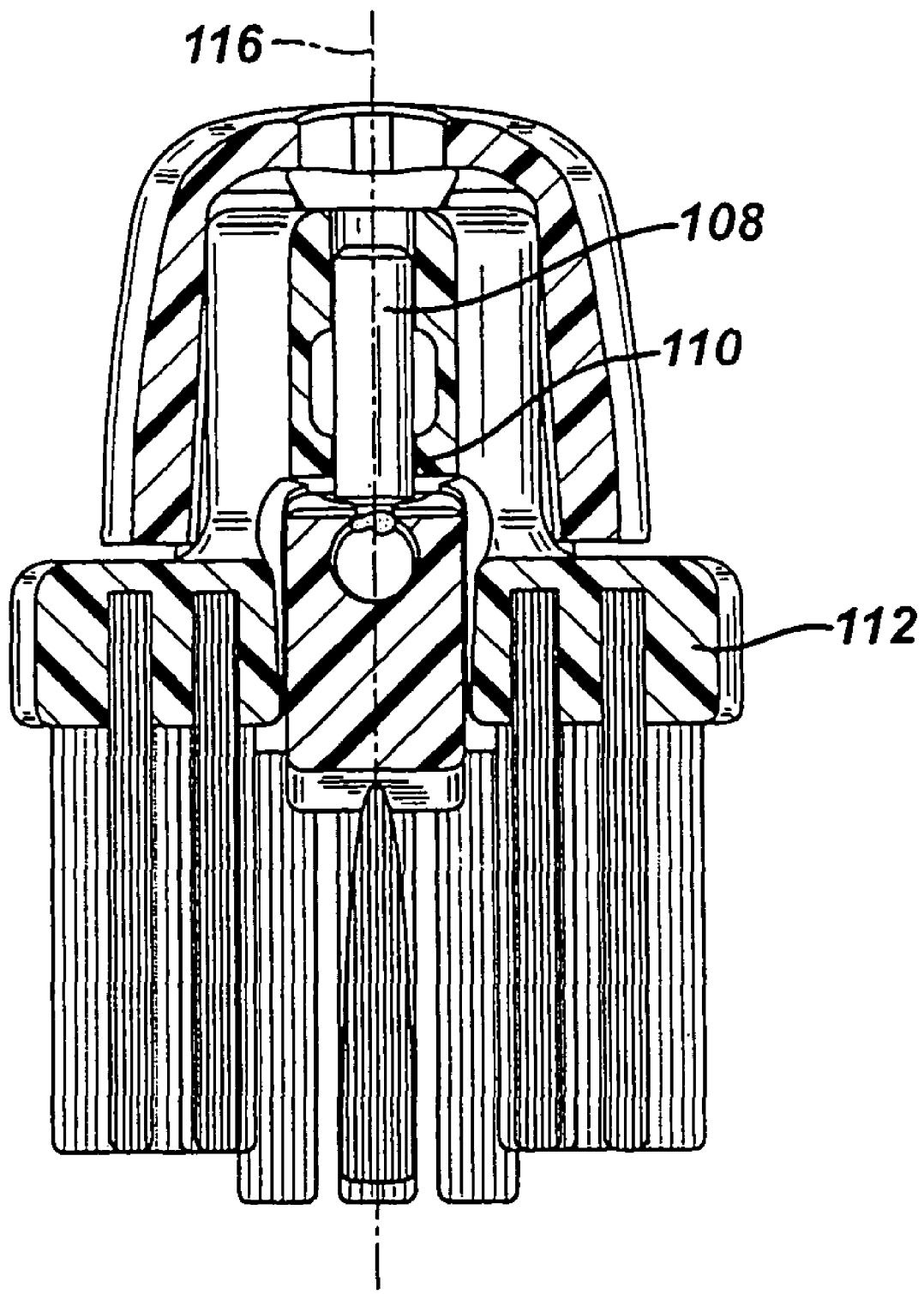
FIG. 12 is a sectional view of FIG. 8 taken along the lines 12-12.

Operation of support 14 will be explained with reference to FIGS. 2, 3A and 3B. Pin 36 is oscillated about its long axis by a drive mechanism (not shown) in neck 12. The drive mechanism can be of conventional design. Oscillation of pin 36 causes brush base 24 and bristles 16 to oscillate in a rotary pattern. Pin 30 retains base 24 within housing 34. Oscillation of base 24 causes core 20 and probe 18 to oscillate with the base because pins 22 ride in track 28 of the base. Pins 22 also ride in respective tracks 26 in the housing, thus causing core 20 and probe 18 to move up and down relative to bristles 16 during oscillation of brush base 24. FIGS. 3A and 3B show that a preferred extension of probe 18 from its lowest to highest position is about 5 mm.

In an alternative embodiment, all of bristles 16 are eliminated, leaving only probe 18 for cleaning teeth. This embodiment would be used primarily for cleaning interdental spaces, not for cleaning the other surfaces of teeth.

Turning to FIGS. 4-7, a second embodiment of the invention will be described. A brushhead 40 can be attached to a handpiece (not shown) of an electric toothbrush. A driveshaft (not shown) protrudes out of the handpiece and can effect an oscillating rotation. Brushhead 40 includes a tube 42 in which a shaft 44 is located. The rear end of tube 42 fits into the housing (not shown) of the handpiece. Shaft 44 engages the driveshaft of the handpiece. A pin 46 is press fitted into shaft 44. Pin 46 can rotate at its free end in a bearing hole 48 in a front part 50 of tube 42. Axis 52 of pin 46 coincides with the axis of the driveshaft of the handpiece.

A pivot 54 can rotate in a bearing hole 56 situated in front part 50 of tube 42. Pivot 54 is retained in hole 56 by a ring 58. A first brush member comprising a brush base 60 is press fitted onto pivot 54. Brush base 60 has a first brush support surface 61 with holes 62 in which tufts of bristles 64 are secured. A cross pin 66 is welded onto the free end of pivot 54. Both ends of cross pin 66 retain brush base 60 on pivot 54 by interaction with a shoulder 68 of the brush base. The central part of cross pin 66 is placed in a bearing hole 70 of a second brush member comprising a pivot arm or rocker 72. Rocker 72 can swivel about cross pin 66 and has a second brush support surface 71 which contains holes 74 in which tufts of bristles 76 are secured.

The pivot arm or rocker 72 comprises a first arm 73 and a second arm 75 which define a first portion 77 and a second portion 79 of the second brush support surface 71. The first portion 77 and the second portion 79 of the second brush support surface 71 are joined together and have free ends 81 and 83 which are spaced apart. The first portion 77 and the second portion 79 of the second brush support surface 71 are capable of pivoting relative to the first brush support surface 61 of the brush base 60 about an axis of cross pin 66 which extends transversely to a longitudinal axis of the head 40 and laterally across the pivot arm or rocker 72.

Shaft 44 includes a bearing hole 78 in which a drive rod 80 can move. The distance between axis 52 of pin 46 and an axis 82 of drive rod 80 is a radius r1. A stud 84 is welded onto the free end of drive rod 80. The distance between an axis 86 of pivot 54 and an axis 88 of stud 84 is a radius r2. Stud 84 can move in a bearing seat 90 in brush base 60. At one end of stud 84 is carried a ball 92 which can move in a cylindrical slot 94 in rocker 72.

When shaft 44 is oscillated about axis 52 through an angle of +−alpha 1 about pin 46, two different motions are induced. First, brush base 60 and rocker 72 are oscillated in a rotating manner through an angle of +−beta 1 about pivot 54 in bearing hole 56. This oscillating rotation causes bristles 64 to wipe plaque off teeth like a broom. Second, rocker 72 is oscillated in a rotating manner through an angle of +−gamma 1 about cross pin 66 in bearing hole 70. Oscillation of rocker 72 about pin 66 causes bristle tufts 76 to loosen plaque like a chisel. Two cycles of oscillation of rocker 72 about pin 66 occur for every one cycle of oscillation of base 60 and rocker 72 about pivot 54. The relations between the oscillation angles alpha 1 to beta 1 and alpha 1 to gamma 1 depend only on radii r1 and r2.

Referring to FIGS. 8-12, a third embodiment of the invention will be described. The third embodiment modifies the relationship between the oscillation angles, primarily to increase the gamma angle of the oscillating rotation of rocker 72. The basic features of the third embodiment remain unchanged from the second embodiment. The main difference is in the location of the drive rod.

In the mid-position of the oscillating rotation of a shaft 100, a drive rod 102 is located at a distance e from a median plane 104 of a brushhead 106. A stud 108 is welded laterally on a free end of drive rod 102 with a distance e between the center-lines. Stud 108 is movable in a bearing seal 110 of a brush base 112. When a drive shaft 114 is in a mid-oscillation position, stud 108 is in a median plane 116 of brush base 112. Drive rod 102 can move in a bearing hole 118 in shaft 114. Bearing hole 118 is situated in the distance e from median plane 104 of shaft 114 when the shaft is in its mid-oscillation position.

When shaft 114 is oscillated about median plane 104 through an angle of +−alpha 1, two different motions are induced. First, brush base 112 and rocker 72 are oscillated in a rotating manner through an angle of +−beta 2 which is smaller than +−beta 1 about axis 120. Second, rocker 72 is oscillated in a rotating manner through an angle of +−gamma 2 which is bigger than +−gamma 1 about cross pin 66. The relations between the oscillation angles alpha 1 to beta 2 and alpha 1 to gamma 2 depend on radii r1 and r2 as well as on the distance e.

In embodiments 2 and 3 of the invention, one component of the rocking motion of rocker 72 causes bristles 76 to move up and down (i.e. substantially parallel to pivot 54) relative to bristles 64.

Figure 13:
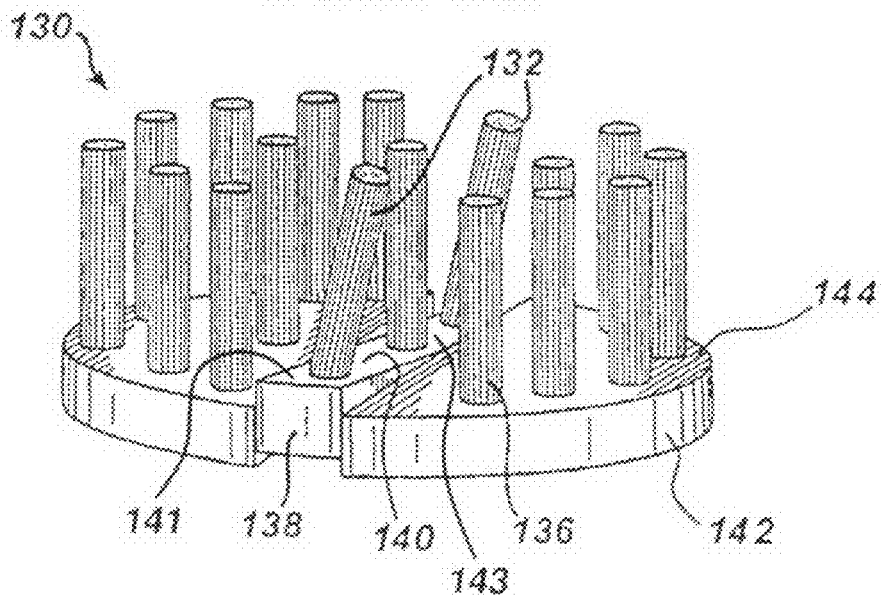
FIG. 13 is a perspective view of a fourth embodiment of a toothbrush head.
Figure 14:
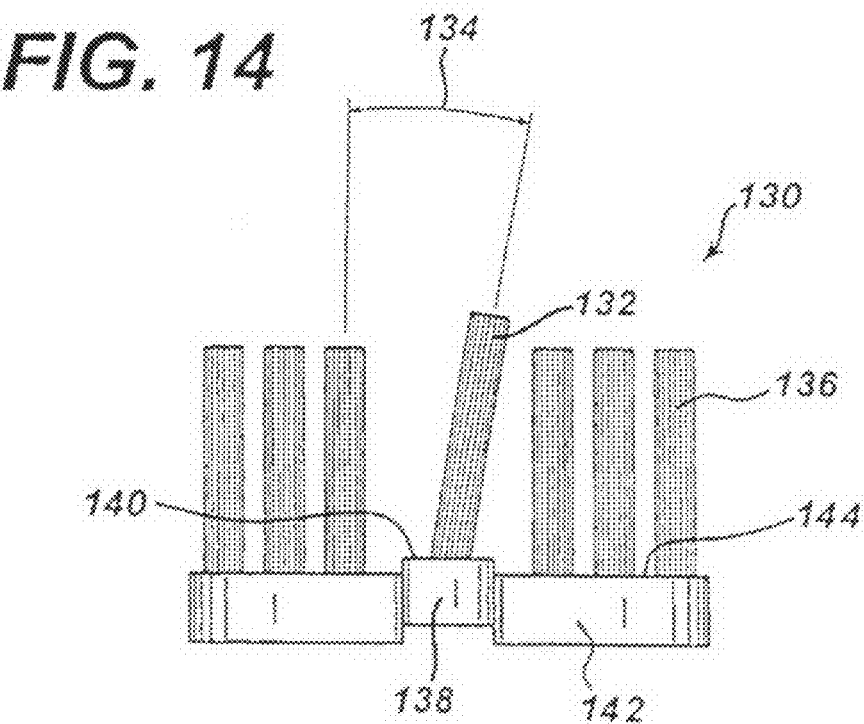
FIG. 14 is a front view of the toothbrush head of FIG. 13.

FIGS. 13 and 14 disclose a toothbrush head 130 which is similar in function to the head of FIG. 4. The major difference is that tufts of bristles 132 on a pivot bar 138 are tilted away from the perpendicular (to the top surface 140 of the pivot bar 138) at an angle 134 of between about 1-20 degrees. Preferably the bristles 132 are tilted along the direction of oscillation of bristles 136 on a brush base 142. Such tilting of bristles 132 provides better interdental penetration during the respective upstrokes of pivot bar 138, particularly for the tuft(s) on bar 138 which are being moved by head 130 in the tilt direction. It is preferable that tufts of bristles on both sides of bar 138 have the same tilt angle and are tilted in the same direction (i.e. in the same plane). Alternatively, tufts of bristles on opposite sides of the bar can be tilted in opposite directions. As shown in FIGS. 13 and 14, when pivot bar 138 is oscillated relative to brush base 142, the top surface 140 of pivot bar 138 and the top surface 144 of brush base 142 are capable of lying in substantially a same plane (when pivot bar 138 is aligned with brush base 142) during the operation of the electric toothbrush.

The brush support surface 140 of the pivot bar 138 includes a first portion 141 and a second portion 143 which are joined together and have free ends which are spaced apart. The first portion 141 and the second portion 143 of the brush support surface 140 are capable of pivoting relative to the brush support surface 144 of the brush base 142 about an axis which extends transversely to a longitudinal axis of the head 130 and laterally across the pivot bar 138.

The invention has been described with reference to several embodiments including a preferred embodiment. However, it will be appreciated that variations and modifications can be effected by a person of ordinary skill in the art without departing from the scope of the invention.

The invention claimed is:

1. An elongated toothbrush head defining a longitudinal axis, said toothbrush head comprising:
   a first brush member having a first brush support surface;
   a second brush member comprising a pivot arm mounted for pivotal movement on the first brush member, the pivot arm having a second brush support surface including a first portion and a second portion, the first portion and the second portion of the second brush support surface being joined together and having free ends which are spaced apart;

the first portion and the second portion of the second brush support surface being capable of pivoting relative to the first brush support surface about an axis which extends transversely to the longitudinal axis of the head and laterally across the pivot arm; and one or more teeth cleaning elements projecting from the first portion and the second portion and inclined at an angle to the second brush support surface.

2. The toothbrush head of claim 1, wherein:
the first portion and second portion of the second brush support surface are spaced apart longitudinally.

3. The toothbrush head of claim 1, wherein:
the teeth cleaning elements on the first portion and the second portion are inclined at an acute angle to the second support surface.

4. The toothbrush head of claim 3, wherein:
the first brush support surface has one or more teeth cleaning elements mounted substantially perpendicular to the first brush support surface.

5. The toothbrush head of claim 3, wherein:
the teeth cleaning elements on the first portion and the second portion are inclined in the same direction.

6. The toothbrush head of claim 3, wherein:
the teeth cleaning elements on the first portion and the second portion are inclined in opposite directions.

7. The toothbrush head of claim 3, wherein:
the teeth cleaning elements comprise at least one tuft of bristles adjacent to the free end of the first portion and at least one tuft of bristles adjacent to the free end of the second portion which are inclined in the same direction.

8. The toothbrush head of claim 3, wherein:
the teeth cleaning elements comprise at least one tuft of bristles adjacent to the free end of the first portion and at least one tuft of bristles adjacent to the free end of the second portion which are inclined in opposite directions.

9. The toothbrush head of claim 3, wherein:
the teeth cleaning elements on the first brush support surface comprise a plurality of bristle tufts which are substantially perpendicular to the first brush support surface.

10. The toothbrush head of claim 3, wherein:
the teeth cleaning elements on the first portion and the second portion are inclined away from a line perpendicular to the second brush support surface at an angle of about 1 to 20 degrees.

* * * * *